US 7,428,296 B2

(12) United States Patent
Bernhardt et al.

(10) Patent No.: US 7,428,296 B2
(45) Date of Patent: Sep. 23, 2008

(54) MEDICAL IMAGING SYSTEM WITH A PART WHICH CAN BE MOVED ABOUT A PATIENT AND A COLLISION PROTECTION METHOD

(75) Inventors: Philipp Bernhardt, Forchheim (DE); Jan Boese, Eckental (DE); Marcus Pfister, Bubenreuth (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 147 days.

(21) Appl. No.: 11/437,090

(22) Filed: May 19, 2006

(65) Prior Publication Data
US 2006/0274888 A1 Dec. 7, 2006

(30) Foreign Application Priority Data
May 19, 2005 (DE) .................. 10 2005 023 165

(51) Int. Cl.
*H05G 1/54* (2006.01)
*H05G 1/02* (2006.01)
(52) U.S. Cl. .................. 378/117; 378/196; 378/197
(58) Field of Classification Search ............. 378/117, 378/196, 197, 204, 206, 65, 62; 600/407, 600/473, 476
See application file for complete search history.

(56) References Cited

U.S. PATENT DOCUMENTS

| 5,485,502 | A  | * | 1/1996 | Hinton et al. ............... 378/117 |
| 6,272,368 | B1 |   | 8/2001 | Alexandrescu |
| 6,590,669 | B1 |   | 7/2003 | Wagner |
| 7,046,765 | B2 | * | 5/2006 | Wong et al. ................. 378/117 |
| 7,280,633 | B2 | * | 10/2007 | Cheng et al. ................. 378/65 |
| 7,319,739 | B2 | * | 1/2008 | Heismann ................... 378/62 |

FOREIGN PATENT DOCUMENTS

| DE | 36 04 955 A1 | 8/1987 |
| DE | 43 35 301 C1 | 12/1994 |
| DE | 197 43 500 A1 | 4/1999 |
| DE | 102 58 130 A1 | 6/2004 |
| EP | 0 372 241 A2 | 6/1990 |

* cited by examiner

*Primary Examiner*—Irakli Kiknadze

(57) ABSTRACT

The invention relates to a medical imaging system as well as a collision protection method for such a system. In this system the movement of a moveable part, e.g. a C-arm, is stopped or slowed down, if the part enters an individual protective zone enclosing the patient. This zone is calculated individually for each patient from the surface of the patient detected by an optical sensor.

20 Claims, 1 Drawing Sheet

MEDICAL IMAGING SYSTEM WITH A PART WHICH CAN BE MOVED ABOUT A PATIENT AND A COLLISION PROTECTION METHOD

CROSS REFERENCE TO RELATED APPLICATIONS

This application claims priority of German application No. 10 2005 023 165.9 filed May 19, 2005, which is incorporated by reference herein in its entirety.

FIELD OF THE INVENTION

The invention relates to a medical imaging system with a part which can be moved about a patient and in particular a system, with which the movement of the moveable part is controlled by a control module which stops or slows down the movement when the part enters a protective zone enclosing the patient. The invention likewise relates to a collision protection method for such an imaging system.

BACKGROUND OF THE INVENTION

In the prior art, medical imaging systems, in particular x-ray systems are known, which are characterized by a great flexibility in the movements of the image recording devices about the patient. In the case of an x-ray system, these moveable parts are in particular the x-ray detector and the x-ray tube. The so-called C-arm x-ray systems particularly enjoy great popularity, in which the x-ray tube and the detector are fixed in each instance to opposing arms of a C-arm, which can be moved arbitrarily about the patient in order to allow x-ray recordings from any projection direction. By varying the distance between the x-ray detector and the patient, the enlargement can furthermore be changed and the image distorting scattered radiation can be minimized. Systems such as Siemens AG's AXIOM Artis for instance are used in particular as angiography systems. Quasi-tomographical 3D images are increasingly generated with such x-ray devices, with which the C-arm is moved about the patient through approximately 180°. With a cycle of this type, also referred to as DynaRun, some of the moveable parts are rotated about the patient at a considerable speed. One problem with these types of imaging systems with moveable parts is that the moveable parts may collide with the patient. Protective mechanisms must thus be introduced in order to rule out any risks to the patient.

With the above-cited AXION Artis system, a protective zone enclosing the patient is defined for instance. If a C-arm approaches this protective zone, it is clearly slowed down so as to avoid the risk of a collision. This protective zone is identical for all patients and has roughly the form of an ellipsoid arranged over the patient support. With thin patients in particular, this protective zone is thus often distanced far from the actual patient surface. It thus often takes an unnecessarily long time to start a specific angulation of the C-arm.

In the case of devices made by Philips, some of the capacitative sensors which detect the proximity of the patient and thereupon slow down the movement of the C-arm are positioned on the C-arms. However, these sensors only have a minimal coverage, so that the movement of the C-arm is also assumed to be slowed down here when it enters an accepted protective zone.

As a final safety feature, both systems have mechanical position indicators, which immediately stop the movement of the moveable parts when a patient is actually contacted.

SUMMARY OF THE INVENTION

The object addressed by the invention is thus to provide a medical imaging system with a faster, more accurate and simpler collision protection system, as well as a corresponding collision protection method. The invention achieves this object with the characterizing features of the claims. Preferred embodiments of the imaging system and collision protection method according to the invention are specified in each instance in the dependent claims.

In accordance with the invention, an optical sensor for detecting the surface of the patient is provided with a medical imaging system, with the imaging system being designed so as to calculate an individual protective zone for this patient from the detected surface of the patient. As known from the prior art, the movement of the moveable part can be stopped or slowed down by a control module when the part enters this protective zone. Since this protective zone takes account of the precise shape of the patient, which was determined by the optical surface detection, a considerably enlarged movement margin of the moveable part is thus enabled. The individual protective zone can begin for instance at a predetermined distance to the measured patient surface, e.g. at a distance of 2 to 6 cm. By way of example, an "envelope" is placed around the shape of the patient measured using the optical surface detection for instance, said "envelope" very accurately reproducing the necessary protective distance to a patient.

The optical sensor preferably comprises a light source and at least one camera. Optical sensors of this type are available from 3D-SHAPE GmbH and are based on the projection of striped patterns. The patterns are projected onto the object to be detected by means of a projector from a first direction and are viewed from another direction with a camera. The stripes appear more or less deformed to the camera, depending on the shape of the viewed object. The shape of the object can also be concluded from the deformation of the stripes. Preferably more than 3 striped patterns are projected, with the intensity of the stripes assuming a sinusoidal pattern. A second camera can be provided to detect 2 sides of the object simultaneously.

This method for optical surface detection, also known as shape detection, is described in DE 102 58 130 A1 for instance. This publication, the disclosure of which is herewith included in this patent application, also describes a method, which is referred to as "shape from shading". With this method, the shape of the mapped object is concluded from the variation in the brightness in an image. If the photograph of a face is examined for instance, brightness variations are determined, although it can be assumed that the reflection coefficient of the skin hardly changes. Instead these brightness variations result from certain parts of the surface being oriented in such a way that they radiate more light to the camera than others. If the light from a light source strikes the surface at a right angle, the brightness is at a maximum, while with glancing incidence it is at a minimum. The contour can be determined from these differences.

Further methods for optical shape detection of objects are described in U.S. Pat. No. 6,590,669 B1 and EP 0 372 241 A1. Any suitable optical sensor system and/or method for optical surface detection can, in principle, be used for the present imaging system and collision protection method. The above-mentioned system from 3D-SHAPE GmbH, with which the object to be measured, in this instance the patient, is illuminated with a striped pattern, is particularly preferable. As only a relatively rough resolution of the measured surface is required for the purpose of the present application, the patient surface can be detected in a period of one or a few seconds up to approximately 1 minute.

A 3D-model of the patient is preferably created from the patient surface detected in this way. This model can for instance map the surface approximated from triangles.

This model is then preferably registered with the coordinate system of the moveable part of the imaging system so as to be able to correspondingly control the movement of the moveable part. To enable this registration, the coordinate system of the imaging system and that of the optical sensor are preferably calibrated spatially to one another. This means that the spatial position and orientation of the two devices are known to one another. In more precise terms, this means that the relation of the coordinate source of the coordinate system of the optical sensor and that of the coordinate source of the coordinate system of the imaging system are known to one another. The following exemplary embodiments exist in respect of the spatial arrangement of the optical sensor relative to the imaging system:

According to a first embodiment, the optical sensor is fixed permanently to the moveable part; in the case of a C-arm x-ray system thus with a C-arm. In this case, the calibration can already be carried out by the factory during the manufacture of the imaging system. If the imaging system is arranged in an examination room in a stationary manner, it is also possible to arrange the optical sensor at a fixed position (stationary) within this room, to mount it for instance on the ceiling. In this case, the spatial relationship between the sensor and the imaging system must only be determined once, e.g. during the assembly of the imaging system by means of calibration. Possible changes, e.g. rotating the optical sensor on its anchorage, can be acknowledged via rotating sensors, whereby an automatic update of the spatial relationship of the two coordinate systems is carried out.

According to a third embodiment, the optical sensor is arranged at the imaging system in a moveable manner. In this case, the optical sensor is arranged either in a mobile manner, e.g. on a stand which can be moved freely within the room, or similarly an infusion stand or the imaging system is mobile or both components are mobile. With this embodiment, the calibration of the spatial relationship of the two coordinate systems can be carried out by means of position/orientation sensors, which are mounted both on the optical sensor as well as on imaging system, in particular on the moveable part such as the C-arm, so as to determine the position of the two devices in respect of one another. Such position/orientation sensors use static or low frequency magnetic fields for instance.

A preferred application of the invention are C-arm x-ray systems, in which the moveable part is an x-ray detector and/or an x-ray tube, which is fixed in each instance to opposing arms of a C-arm. The optical surface detection and the calculation of the individual protective zone can be carried out in each instance prior to the recording of image data, in particular prior to an image-controlled diagnostic or surgical intervention and/or periodically during the intervention. The collision protection method is preferably repeated after a patient movement. The surface detection and calculation of the protective zone can also be carried out during a DynRun, so as to interrupt the scan during acute patient movements in order to reduce the dose. This presumes that the optical sensor operates rapidly enough and that the optical surface detection is completed within approximately 1 to 10 seconds, particularly within 5 seconds.

BRIEF DESCRIPTION OF THE DRAWINGS

An exemplary embodiment of the invention is now described with reference to the accompanying drawings, in which.

DETAILED DESCRIPTION OF THE INVENTION

Figure 1:
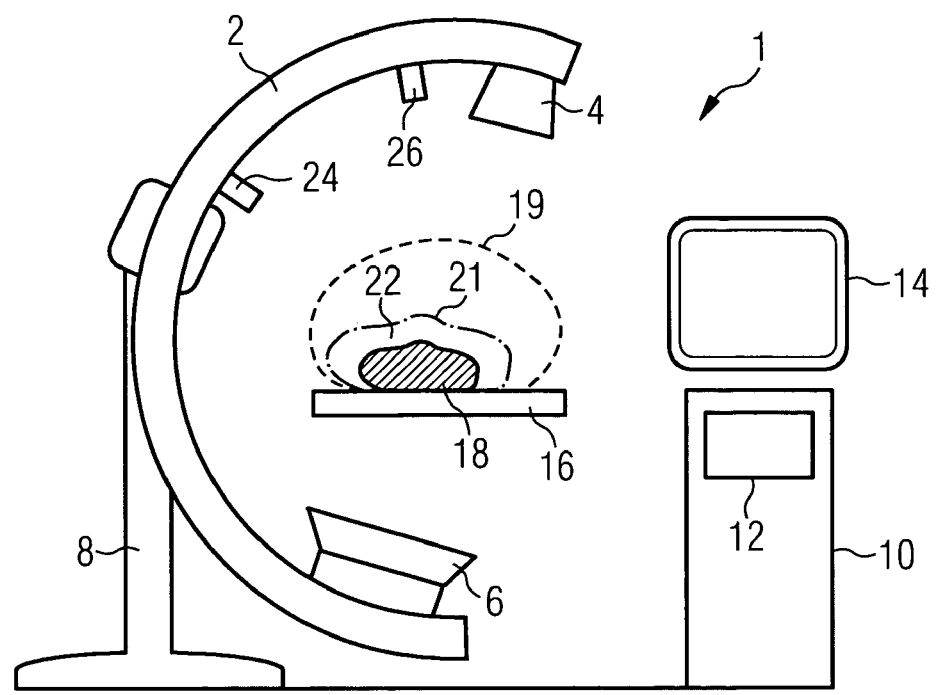
FIG. 1 shows a schematic view of a medical imaging system according to an exemplary embodiment of the invention with a cross-sectional illustration of the patient and FIG. 2 shows a schematic view of a 3D model of the patient calculated using an exemplary embodiment of the method according to the invention.

FIG. 1 shows a C-arm x-ray device 1 with a C-arm 2, at whose opposing arms an x-ray tube 4 and an x-ray detector 6 are fixed in each instance. The C-arm can be moved about a patient support 16 and is suspended on the stand 8 in a moveable fashion for this purpose. The electric motors effecting the movement of the C-arm are not shown. This movement is controlled by the control module 12, which can form part of a control and image processing computer 10. The x-ray images recorded using the imaging system 1 can be displayed on the screen 14. The patient 18 is shown on the support 16 as a hatched surface. The dashed line 19 circumscribes an ellipsoid, which represents the envelope for the protective zone around the patient in the case of imaging systems according to the prior art. As can be seen from the drawing, the envelope 19 is considerably wider and higher than the patient shown, as it is not tailored to this specific patient, but is instead intended to offer adequate protection for all conceivable and also all overweight patients.

A projector 24 and a camera 26 are further fixed to the C-arm 2, which together form the optical sensor. As described above, the projector 24 can illuminate the patient with a striped pattern, which is viewed by the camera 26 from a lateral direction. The surface shape of the patient 18 can be calculated for instance from the displacement of the stripes resulting from the contour of the patient, and likewise from the control computer 10 for instance.

This surface shape which was determined by the optical sensor with a resolution of approximately 1 mm to 4 cm, preferably with a resolution of approximately 1 to 2 cm, is then used to place an individual envelope 21 around the patient 18, shown in the drawing with a dashed line. This envelope has an average distance of 5 cm to the patient for instance, but must not follow the patient surface exactly as is also obvious from FIG. 2. The individual protective zone 22 for this patient is enclosed by this envelope 21. The envelope 21 is calibrated with the coordinate system of the C-arm, so that the control computer 10 can control the movements of the C-arm such that neither the x-ray tube 4 nor the detector 6 enter the protective zone 22, or such that the movement is significantly slowed down when the individual protective zone is crossed. If one of the moveable parts however crosses an area lying outside the protective zone 22, said area lying within the ellipsoid 19, the movement does not need to be slowed down.

The surface detection can be carried out once in each instance prior to an examination or an image-controlled intervention to the patient and/or repeated if necessary during the examination and/or the intervention.

Figure 2:
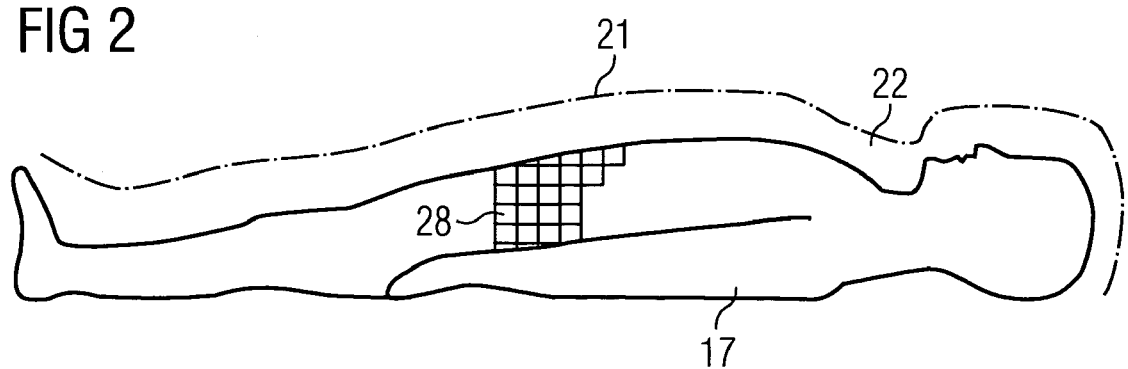

FIG. 2 shows a schematic representation of a model 17 of a patient, which was created using the optical surface detection. Individual pixels are indicated with 28, from which the model is composed. Alternatively, the 3D model can also be spanned by a triangular surface. According to another alternative, the patient surface can also be detected in each instance as a silhouette, with the envelope 21 being placed in each instance about the silhouette. Patient silhouettes are preferably recorded here from several lines of vision. The envelope 21 reproduces the protective distance to the patient very accurately. It is also not bound to particular shape models and in contrast to ellipsoid models, thus takes account of a protruding arm or suchlike.

The imaging system and collision protection method according to the invention thus allow both an improved protection of the patient and also an improvement in the workflow. The latter results from fewer reductions in speed of the C-arm movement being necessary when the assumed protective zone is approximated, if the precise size and shape of the patient are known.

The invention claimed is:

1. A medical imaging system with a movable part that moves about a respective patient, comprising:
    a control module for controlling the movable part;
    an optical sensor for detecting a surface of the respective patient, wherein said surface defines an envelope uniquely corresponding to the respective patient; and
    a computing device for calculating an individualized protective zone for the respective patient based on the envelope of the respective patient,
    wherein a movement of the moveable part is stopped or slowed when the movable part enters into the individualized protective zone for the respective patient.

2. The medical imaging system as claimed in claim 1, wherein the optical sensor comprises a light source and a camera.

3. The medical imaging system as claimed in claim 2, wherein the light source is a projector which illuminates a patient with a striped pattern to detect a surface of the patient.

4. The medical imaging system as claimed in claim 1, wherein the medical imaging system is an x-ray system and the moveable part is an x-ray detector or an x-ray tube.

5. The method as claimed in claim 4, wherein the x-ray system is a C-arm system and the x-ray detector and the x-ray tube are fixed to a C-arm of the C-arm system.

6. The medical imaging system as claimed in claim 5, wherein the optical sensor is fixed to the C-arm.

7. The medical imaging system as claimed in claim 1, wherein the optical sensor is arranged stationary or moveably within an examination room in which the medical imaging system is located.

8. The medical imaging system as claimed in claim 1, wherein a coordinate system of the medical imaging system and a coordinate system of the optical sensor are spatially calibrated with respect to each other.

9. The medical imaging system as claimed in claim 1, wherein the medical imaging system creates a 3D-model of the patient from the detected surface of the patient and registers the 3D-model of the patient with a coordinate system of the medical imaging system.

10. The medical imaging system as claimed in claim 1, wherein the individualized protective zone encloses the patient.

11. A collision protection method for a medical imaging system with a movable part that moves about a respective patient to prevent a collision of the moveable part with the patient, comprising:
    detecting an optical surface of the respective patient by an optical sensor, wherein said surface defines an envelope uniquely corresponding the respective patient; and
    calculating an individualized protective zone for the respective patient based on the envelope of the respective patient,
    wherein a movement of the moveable part which is controlled by a control module is stopped or slowed when the movable part enters into the individualized protective zone enclosing the patient.

12. The collision protection method as claimed in claim 11, wherein the optical sensor comprises a light source and a camera.

13. The collision protection method as claimed in claim 12, the light source is a projector which illuminates a patient with a striped pattern to detect an optical surface of the patient.

14. The collision protection method as claimed in claim 11, wherein the optical surface detection and the calculation of the individualized protective zone is carried out prior to or during a recording of an image data of the patient.

15. The collision protection method as claimed in claim 11, wherein the optical surface detection and the calculation of the individualized protective zone is repeated after a movement of the patient.

16. The collision protection method as claimed in claim 11, wherein a coordinate system of the medical imaging system and a coordinate system of the optical sensor are spatially calibrated with respect to each other prior to a recording of an image data of the patient.

17. The collision protection method as claimed in claim 11, wherein a 3D model of the patient is created based on the detected optical surface of the patient and the individualized protective zone is calculated based on the 3D model of the patient.

18. The collision protection method as claimed in claim 11, wherein the individualized protective zone encloses the patient.

19. A medical imaging system with a movable part that moves about a patient, comprising:
    a control module for controlling the movable part;
    a sensor for detecting a surface of the patient, wherein said surface defines an envelope uniquely corresponding to the respective patient; and
    a computing device for calculating an individualized protective zone for the patient based on the envelope of the patient,
    wherein a movement of the moveable part is stopped or slowed when the movable part enters into the individualized protective zone.

20. The medical imaging system as claimed in claim 19, wherein the sensor is an optical sensor.

* * * * *